US008591952B2

(12) United States Patent
Stellacci et al.

(10) Patent No.: US 8,591,952 B2
(45) Date of Patent: Nov. 26, 2013

(54) ABSORBANT SUPERHYDROPHOBIC MATERIALS, AND METHODS OF PREPARATION AND USE THEREOF

(75) Inventors: Francesco Stellacci, Somerville, MA (US); Jing Kong, Winchester, MA (US); Xiaogang (Bruno) Liu, Weymouth, MA (US); Jikang Yuan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 940 days.

(21) Appl. No.: 12/445,142

(22) PCT Filed: Oct. 9, 2007

(86) PCT No.: PCT/US2007/021569
§ 371 (c)(1),
(2), (4) Date: Dec. 22, 2009

(87) PCT Pub. No.: WO2008/045433
PCT Pub. Date: Apr. 17, 2008

(65) Prior Publication Data
US 2010/0086604 A1 Apr. 8, 2010

Related U.S. Application Data

(60) Provisional application No. 60/850,259, filed on Oct. 10, 2006.

(51) Int. Cl.
*A61K 9/14* (2006.01)
*B01J 20/28* (2006.01)
(52) U.S. Cl.
CPC .......... *A61K 9/14* (2013.01); *A61L 2400/12* (2013.01); *B01J 20/28007* (2013.01); *C01P 2004/16* (2013.01); *Y10S 210/922* (2013.01); *Y10S 524/917* (2013.01); *Y10S 977/762* (2013.01)
USPC ........... 424/489; 428/222; 428/378; 428/379; 428/375; 428/391; 210/767; 210/922; 524/917; 977/762
(58) Field of Classification Search
None
See application file for complete search history.

(56) References Cited

U.S. PATENT DOCUMENTS

| 3,562,153 | A | 2/1971 | Tully et al. |
| 5,203,778 | A | 4/1993 | Boehringer |
| 5,358,990 | A | 10/1994 | Woodard |
| 5,368,892 | A | 11/1994 | Berquier |
| 6,517,802 | B1 * | 2/2003 | Xiao et al. ................ 423/592.1 |
| 6,852,390 | B2 | 2/2005 | Extrand |
| 2002/0130311 | A1 * | 9/2002 | Lieber et al. ...................... 257/1 |
| 2005/0263456 | A1 * | 12/2005 | Cooper et al. ................ 210/660 |
| 2006/0049101 | A1 * | 3/2006 | Suib et al. ................ 210/500.21 |
| 2006/0159916 | A1 | 7/2006 | Dubrow et al. |

FOREIGN PATENT DOCUMENTS

| WO | WO 01/03208 | 1/2001 |
| WO | WO 02/17362 | 2/2002 |
| WO | WO 02/48701 | 6/2002 |
| WO | WO 2005/005566 A2 | 1/2005 |

OTHER PUBLICATIONS

AP Graham, GS Duesberg, W Hoenlein, F Kreupl, M Liebau, R Martin, B Rajasekharan, W Pamler, R Seidel, W Steinhoegl, E Unger. "How Do Carbon Nanotubes Fit Into the Semiconductor Roadmap." Applied Physics A: Materials Science & Processing, vol. 80, 2005, pp. 1141-1151, Published Online Mar. 11, 2005.*
J Yuan, X Liu, O Akbulut, J Hu, SL Suib, J Kong, F Stellacci. "Superwetting nanowire membranes for selective absorption." Nature Nanotechnology, vol. 3, Jun. 2008, pp. 332-336.*
EA Thomson. "MIT Develops a 'Paper Towel' for Oil Spills." http://web.mit.edu/newsoffice/2008/oil-paper-0530.html?tmpl=component&print=1, accessed Oct. 3, 2012, published Jun. 4, 2008, 2 printed pages.*
P. Patel. "Nano Sponge for Oil Spills." Technology Review, Jun. 2, 2008, http://www.technologyreview.com/news/410204/nano-sponge-for-oil-spills/, accessed Oct. 3, 2012, 5 printed pages.*

* cited by examiner

*Primary Examiner* — Frederick Krass
*Assistant Examiner* — Isaac Shomer
(74) *Attorney, Agent, or Firm* — Mark S. Cohen; Pearl Cohen Zedek Latzer Baratz, LLP (57) ABSTRACT

The present invention relates to coated, absorbent, freestanding assemblies comprising inorganic nanowires, articles of manufacture comprising the same, processes of producing the same and methods of use thereof. The assemblies of this invention are useful in various applications, including removal of organics or hydrophobic materials, and waterproofing applications.

15 Claims, 6 Drawing Sheets

ABSORBANT SUPERHYDROPHOBIC MATERIALS, AND METHODS OF PREPARATION AND USE THEREOF

CROSS-REFERENCE TO RELATED APPLICATIONS

This application is a National Phase Application of PCT International Application No. PCT/US07/21569, International Filing Date Oct. 9, 2007, claiming priority of U.S. Provisional Patent Application No. 60/850,259, filed Oct. 10, 2006, all of which are incorporated herein by reference in their entirety.

FIELD OF THE INVENTION

The present invention relates to absorbent nanowire assemblies, methods of producing the same, and applications thereof. The present invention further relates to applications which make use of the interfacial properties and thermal stability of the assemblies, including the development of recyclable absorbent materials.

BACKGROUND OF THE INVENTION

The ability to control interfacial properties, such as wettability, is of great importance in emerging technologies as diverse as protein engineering, microfluidic devices, and antifouling water filtration systems. An extraordinary array of approaches that involve topological construction of micro- and nanostructures, surface modification with low-surface-energy molecules, utilization of stimuli-responsive materials have been developed to alter the wettability of a material. The vast majority of these approaches, however, rely on structures that are firmly coupled to supporting substrates and thus regarded as integrated systems. In contrast, the approach that leads to an easily scalable procedure to create appropriate large-scale free-standing structures for practical applications is a substantial challenge as assembly methods for simultaneous control of features at lengths from the nanometer scale to the macroscale remain elusive. Free-standing membrane structures, such as layer-by-layer assembled polymer films, carbon nanotube membranes and sheets, have been recently reported, but they have limitations for systems that need to require low-cost fabrication, high thermal stability, high levels of control over a wide range of wetting behavior, and high degrees of wetting reversibility.

SUMMARY OF INVENTION

In one embodiment, this invention provides a coated, absorbent, freestanding assembly comprising inorganic nanowires. In one embodiment, the nanowires have a diameter ranging from between 1 nm-1 micron. In one embodiment, the nanowires are assembled in bundles, which in one embodiment, a length of about 200 micrometers to about 10 centimeters. In one embodiment, the nanowires inter-penetrate and form a micro-porous network.

According to this aspect and in one embodiment, the nanowires comprise a metal oxide, which in some embodiments is manganese oxide, which in some embodiments is cryptomelane-type manganese oxide.

In some embodiments, the nanowires comprise a metal alloy. In some embodiments, the nanowires comprise a doped metal ion, which in some embodiments is iron, cobalt, nickel, cadmium, or a combination thereof. In some embodiments, the nanowires comprise a conductive or semi-conductive material.

In some embodiments, the assembly forms a paper or foil.

In some embodiments, the assembly is superhydrophobic. In some embodiments, the assembly is coated with a low surface energy material, which in some embodiments is a fluorocarbon based silane, which in some embodiments is an organosilane. In some embodiments, any hydrophobic material, which can be attached to or associated with the nanowire assemblies of this invention may be used, for example, a hydrophobic material comprising terminal reactive groups. In some embodiments, the low surface energy material is covalently attached to said assembly. In some embodiments, the low surface energy material is non-covalently associated with said assembly.

In some embodiments, the assembly is thermostable. In some embodiments the assembly may be stripped and recoated two or more times.

In some embodiments, this invention provides an article of manufacture comprising an assembly of this invention. In some embodiments, this invention provides a device, apparatus or apparel comprising an assembly of this invention. In some embodiments, the device is a filter or a membrane.

In some embodiments, this invention provides a packaging material comprising an assembly of this invention.

In some embodiments, this invention provides a method of purifying a fluid contaminated with organic materials, the method comprising contacting a solution contaminated with one or more organic materials with a coated assembly of this invention.

According to this aspect and in one embodiment, the method comprises use of a filter or membrane comprising a coated assembly of this invention.

In one embodiment, the organic materials are hydrophobic materials, or in one embodiment, an organic solvent. In one embodiment, the organic material is a petroleum based product.

In one embodiment, this invention provides a method of waterproofing a material, the method comprising surrounding or coating the material with a coated assembly of this invention.

In one embodiment, the assembly is coated with the low surface energy material on a surface distal to the surface in contact with the material. In one embodiment, the proximal surface in contact with the material is bonded to the material.

In one embodiment, the material is a food or pharmaceutical product. In one embodiment, the material is a machinery or apparel, which is submerged in water, which in some embodiments, is subjected to high water pressure.

In one embodiment, this invention provides a method of diminishing or abrogating lipid accumulation in a blood vessel of a subject, the method comprising inserting a removable assembly of this invention in the blood vessel for a period of time sufficient for lipid accumulation to occur on or in the assembly and removing the assembly. According to this aspect and in one embodiment, the method further comprises administering to the subject an agent, which stimulates digestion or release of a lipid from the blood vessel walls.

In another embodiment, this invention provides a process for the preparation of a coated, absorbent, freestanding assembly comprising inorganic nanowires, the process comprising:
  hydrothermally synthesizing inorganic nanowires;
  dispersing said nanowires in a polar solvent to form a suspension;

casting said suspension on a non-adherent substrate to form a freestanding assembly; and coating said freestanding assembly with a low-surface energy molecule.

In some embodiments, the process further comprises removal of hydrophilic liquids, for example by evaporation thereof.

In some embodiments of the process of this invention, the polar solvent is water. In some embodiments, the non-adherent substrate is teflon. In some embodiments, the casting forms a paper or foil.

In some embodiments, the coating results in a covalent attachment of the low-surface energy molecule to a surface of the assembly. In some embodiments, the coating results in the formation of non-covalent associations between the low-surface energy molecule and at least a portion of a surface of the assembly. In some embodiments, the process further comprises stripping of the coating, and subsequent reapplication of the coating, which in some embodiments may be accomplished two or more times. In some embodiments, the stripping of the coating is accomplished by ultrasonication, application of a temperature of at least 300° C., or a combination thereof.

BRIEF DESCRIPTION OF THE DRAWINGS

FIG. 1 demonstrates the characteristics of one embodiment of an $MnO_2$ nanowire of this invention. (A) Optical image of $MnO_2$ nanowire paper. (B) SEM image of cross-sectional area of the nanowire paper, showing a layered structure. (C) Low-magnification SEM image showing surface morphology of the nanowire paper. (D) SEM image of the interpenetrating nanowire networks. (E) High-magnification SEM image of a nanowire bundle. (F) Typical low-magnification TEM image of $MnO_2$ nanowires. (G) TEM image of a single $MnO_2$ nanowire. (H) High magnification TEM image of the nanowire shown in FIG. 1G. (Inset) The corresponding selected-area electron pattern. (I) Optical image of a water droplet from a video contact angle device. (J) Optical image taken after the water droplet completely wets the $MnO_2$ nanopaper.

FIG. 2 demonstrates an embodiment of a coated assembly of this invention. (A) Optical image of a water droplet on organosilane-coated $MnO_2$ paper. (B) SEM image of the organosilane-coated nanowires. (Inset) High-magnification SEM image of an organosilane-coated nanowire bundle. (C) TEM image of as-modified nanowires. (Inset) The corresponding SAED pattern. (D) High-magnification TEM image showing a conformal sheath on the surface of the nanowire. (E) EDS spectrum taken from a selected area marked in FIG. 2D. (F) Representation of the reversible transition between superhydrophilic (top) and superhydrophobic (bottom) states of the $MnO_2$ paper. (G) A series of contact angle and hysteresis measurements taken after each transition cycle. Error bars represent the standard deviation of triplicate measurements.

FIG. 3 demonstrates another embodiment of a coated assembly of this invention. (A) SEM image showing morphology of $Mn_2O_3$ nanowire paper. (B) X-ray powder diffraction pattern of the $Mn_2O_3$ nanowire paper. (C) TEM image of the $Mn_2O_3$ nanowires. (D) TEM image of an organosilane-coated $Mn_2O_3$ nanowire. (E) High-magnification TEM image of the organosilane-coated $Mn_2O_3$ nanowire. (Inset) The corresponding SAED pattern. (F) High-magnification TEM image of the $Mn_2O_3$ nanowires. (Inset) The corresponding SAED pattern. (G) Optical image of a water droplet on the organosilane-coated $Mn_2O_3$ paper.

FIG. 4 demonstrates an embodiment of a method of use of the coated assemblies of this invention. Oil-uptake studies of the organosilane-coated $MnO_2$ nanowire paper. (A) Absorption capacities of the nanowire paper for a selection of organic solvents and oils in terms of its weight gain. (B) and (C) show that a layer of gasoline can be removed by the addition of self-supporting nanowire paper to the gasoline followed by the removal of the paper. The gasoline was labeled with Oil Blue 35 dye for clear presentation.

DETAILED DESCRIPTION OF THE INVENTION

This invention provides, in some embodiments, coated, absorbent, freestanding assemblies comprising inorganic nanowires, uses thereof, and methods of producing the same.

The coated assemblies of this invention are characterized, inter alia, by their tensile strength, flexibility and thermal stability, as well as their superhydrophobicity.

In some embodiments, this invention provides a simple and rapid approach to controlling surface wetting, based on self-assembled free-standing structures of nanowires.

Figure 1:
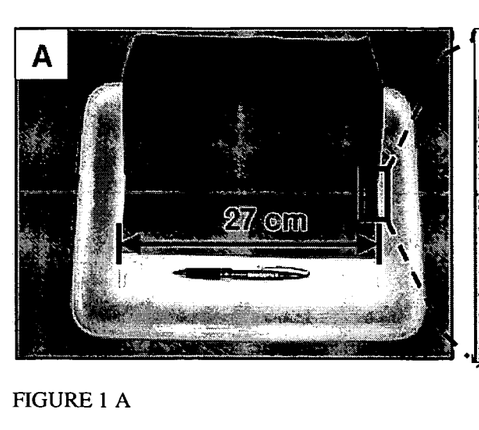

The nanowire assemblies are, in some embodiments, composed of micro- and nanoporous structures that span multiple length scales. In an embodiment exemplified herein the nanowire assembly exhibited a remarkably superhydrophilic phenomenon, which when coated with a thin layer of hydrophobic molecules (e.g.; organosilanes), the e assemblies and their analogues with nanoscale point defects became superhydrophobic, as exemplified herein in FIGS. 1-3.

In some embodiments, the changes in wettability are completely reversible upon coating with or removal of the hydrophobic molecules at elevated temperatures, with in some embodiments, only subtle changes in water contact angles and hystereses observed in each switching cycle, as exemplified herein.

In one embodiment of the invention, the term "contact angle" may refer to the angle on the liquid side tangential line draw through the three phase boundary where a liquid, gas and solid intersect.

In one embodiment of the invention, the term "static contact angle" may refer to the contact angle measured of a Sessile drop on a solid substance when the three phase line is not moving.

In one embodiment of the invention, the term "dynamic contact angle" may be divided into "advancing contact angle" and "receding contact angle" which may refer to, according to embodiments of the invention, to the contact angles measured when the three phase line is in controlled movement by wetting the solid by a liquid or by withdrawing the liquid over a pre-wetted solid, respectively. In another embodiment, the liquid is water.

In one embodiment of the invention, the term "contact angle hysteresis" may refer to the difference between the measured advancing and receding contact angles.

In one embodiment of the invention, the term "wettability" may refer to the process when a liquid spreads on (wets) a solid substrate. In another embodiment wettability may be estimated by determining the contact angle.

In one embodiment, this invention provides a coated, absorbent, freestanding assembly comprising inorganic nanowires.

According to this aspect and in one embodiment, the nanowires may comprise any metal or metal alloy, as well as other appropriate elements, as will be appreciated by one skilled in the art. In one embodiment, the nanowires comprise a metal oxide, which in some embodiments is manganese oxide, which in some embodiments is cryptomelane-type manganese oxide. In some embodiments, the nanowires comprise titanium, zinc, aluminum In some embodiments, the nanowires comprise a metal alloy. In some embodiments, the nanowires comprise a doped metal ion, which in some embodiments comprising doping with iron, cobalt, nickel, copper, or a combination thereof. In some embodiments, the nanowires comprise a conductive or semi-conductive material.

In one embodiment, the term "nanowire" refers to, inter alfa, any elongated conductive or semiconductive material (or other material described herein) that includes at least one cross sectional dimension that is less than 1000 nm, or in some embodiments, less than 750 nm, or in some embodiments, less than 500 nm, or in some embodiments, less than 250 nm, or in some embodiments, less than 150 nm, or in some embodiments, less than 100 nm, or in some embodiments, less than 75 nm. In some embodiments, the nanowires of this invention will have at least one cross sectional dimension that ranges from about 1 nanometer to about 1 micron.

In some embodiments, the nanowires of this invention will have an aspect ratio (length:width) of greater than 10, or in some embodiments greater than 50, or in some embodiments, greater than 100.

The nanowires of this invention, in some embodiments, are substantially homogeneous in material properties, or in certain embodiments are heterogeneous (e.g. nanowire heterostructures).

The nanowires can be fabricated from essentially any convenient material or materials, and can be, e.g., substantially crystalline, substantially monocrystalline, polycrystalline, or amorphous. Nanowires can have a variable diameter or can have a substantially uniform diameter, that is, a diameter that shows a variance less than about 20% (e.g., less than about 10%, less than about 5%, or less than about 1%) over the region of greatest variability and over a linear dimension of at least 5 nm (e.g., at least 10 nm, at least 20 nm, or at least 50 nm). Typically the diameter is evaluated away from the ends of the nanowire (e.g. over the central 20%, 40%, 50%, or 80% of the nanowire). A nanowire can be straight or can be e.g. curved or bent, over the entire length of its long axis or a portion thereof. In certain embodiments, a nanowire or a portion thereof can exhibit two- or three-dimensional quantum confinement. Nanowires according to this invention can expressly exclude carbon nanotubes.

Examples of such nanowires include semiconductor nanowires as described in Published International Patent Application Nos. WO 02/17362, WO 02/48701, and WO 01/03208, which are incorporated herein by reference.

In some embodiments, the nanowires will comprise, inter alfa, a metal such as gold, nickel, palladium, iradium, cobalt, chromium, aluminum, titanium, tin and the like, metal alloys, polymers, conductive polymers, ceramics, and/or combinations thereof.

In some embodiments, the nanowires may comprise a dopant, such as B, Al, In, P, As, Sb, Mg, Zn, Cd, Hg, C, Si, Ge, Sn, Se, Te, or combinations thereof.

In one embodiment, the nanowires are assembled in bundles, which in one embodiment, have a length of about 200 micrometers to about 10 centimeters. In one embodiment, the nanowires, or in some embodiments, the bundles, inter-penetrate and form a micro-porous network, or in some embodiments form a nano-porous network, or in some embodiments for both a micro-porous and nano-porous network. In one embodiment of this invention, the assembly may be composed of wires randomly oriented within a plane.

In some embodiments, the assemblies may be shaped to any configuration desired, as will suit a particular application. Thickness of the assemblies may vary as well, within several orders of magnitude.

In some embodiments, the assembly is superhydrophobic. In some embodiments, the assembly is coated with a low surface energy material, which in some embodiments is a fluorocarbon based silane, which in some embodiments is an organosilane. In some embodiments, the low surface energy material is any hydrophobic material, which can be attached to a nanowire assembly, as herein described. In some embodiments, the hydrophobic material may comprise a terminal reactive group.

In some embodiment, the low surface energy material is a silicone, for example a siloxane. In some embodiments the low surface energy material is a chlorotrifluoroethylene (CTFE oil), a polyphenyl ether, PTFE9 nylon, glass fibers, polyethersulfone, polypropylene, or others. In some embodiments, the low surface energy material is a hydrocarbon, or substituted hydrocarbon. In one embodiment, the hydrocarbon is a fatty acid having at least 12 carbon atoms. In some embodiments, the fatty acid is stearic acid, lauric acid, myristic acid, palmitic acid, oleic acid, linolenic acid or arachidonic acid.

In some embodiments, the low surface energy material may comprise a polyolefin, a styrene polymer, a halogenated hydrocarbon polymer, a vinyl polymer, an acrylic polymer, an actylate polymer, a methacrylic polymer, a methacrylate polymer, a polyester, an anhydride polymer, a polyacrylamide, a cyclo-olefin polymer, a polysiloxane, a polycarbonate, or a copolymer thereof. In some embodiments, the low surface energy material is an aryl, an alkyl, or a halogenated alkyl. In some embodiments, the low surface energy material comprises a mixture or blend of at least two hydrophobic polymers. In another embodiment, the low surface energy material is a modified hydrophobic polymer. In some embodiments, the modified hydrophobic polymer is a modified polyolefin, a modified styrene polymer, a modified halogenated hydrocarbon polymer, a modified vinyl polymer, a modified acrylic polymer, a modified acrylate polymer, a modified methacrylic polymer, a modified methacrylate polymer, a modified polyester, a modified anhydride polymer, a modified polyacrylamide, a modified cyclo-olefin polymer, a modified polysiloxane, a modified polycarbonate, or modified copolymers thereof. In some embodiments, the modification is a covalent modification and/or a partial modification.

In some embodiment, the low surface energy material is a poly(aromatic (meth)acrylates) such as, but not limited to: poly(aryl (meth)acrylates), poly(aralkyl (meth)acrylates), poly(alkaryl (meth) acrylates), poly(aryloxyalkyl (meth) acrylates), and poly (alkoxyaryl (meth)acrylates). In some embodiments the poly(aralkyl (meth)acrylate) can be made from aromatic esters derived from alcohols also containing aromatic moieties, such as benzyl alcohol. In some embodiments the poly(alkaryl (meth)acrylate) can be made from aromatic esters derived from aromatic alcohols such as p-anisole. In some embodiments the poly(aromatic (meth)acrylates) include aryl groups having from 6 to 16 carbon atoms and I with molecular weights from about 50 to about 900 kilodaltons. In some embodiments the poly(aryl (meth)acrylates) include poly(9-anthracenyl methacrylate), poly(chlorophenyl acrylate), poly(methacryloxy-2-hydroxybenzophenone), poly(methacryloxybenzotriazole), poly(naphthyl acrylate), poly(naphthylmethacrylate), poly-4-nitrophenylacrylate, poly(pentachloro(bromo, fluoro) acrylate) and methacrylate, poly(phenyl acrylate) and poly(phenyl methacrylate). In some embodiments the poly(aralkyl (meth)acrylates) include poly(benzyl acrylate), poly(benzyl methacrylate), poly(2-phenethyl acrylate), poly(phenethyl methacrylate) and poly(1-pyrenylmethyl methacrylate). In some embodiments the poly(alkaryl(meth)acrylates) include poly(4-sec-butylphenyl methacrylate), poly(3-ethylphenyl acrylate), and poly(2-methyl-1-naphthyl methacrylate). In some embodiments the poly(aryloxyalkyl (meth)acrylates) include poly(phenoxyethyl acrylate), poly(phenoxyethyl methacrylate), and poly(polyethylene glycol phenyl ether acrylate) and poly(polyethylene glycol phenyl ether methacrylate) with varying polyethylene glycol molecular weights.

In some embodiments the poly(alkoxyaryl(meth)acrylates) include poly(4-methoxyphenyl methacrylate), poly(2-ethoxyphenyl acrylate) and poly(2-methoxynaphthyl acylate).

Acrylate or methacrylate monomers or polymers and/or their parent alcohols are commercially available from, for example, Sigma-Aldrich (Milwaukee, Wis.) or Polysciences, Inc. (Warrington, Pa.).

In some embodiments, the low surface energy material may comprise (i) ethylene copolymers with other alkylenes, (ii) polybutenes, (iii) diolefin-derived, non-aromatic polymers and copolymers, (iv) aromatic group-containing copolymers, (v) epichlorohydrin-containing polymers, (vi) poly (ethylene-co-vinyl acetate), or combinations thereof.

In some embodiments, the low surface energy material may comprise ethylene copolymers with other alkylenes, which in turn, can include straight chain and branched alkylenes, as well as substituted or unsubstituted alkylenes. In some embodiments, the low surface energy material may comprise copolymers prepared from alkylenes that comprise from 3 to 8 branched or linear carbon atoms, inclusive, optionally alkylene groups that comprise from 3 to 4 branched or linear carbon atoms, inclusive, and in some embodiments, the alkylene group contains 3 carbon atoms (e.g., propylene). In various embodiments, the alkylene is a straight chain alkylene (e.g., 1-alkylene).

In some embodiments, the low surface energy material may comprise poly(ethylene-co-propylene), poly(ethylene-co-1-butene), poly(ethylene-co-1-butene-co-1-hexene) and/or poly(ethylene-co-1-octene).

In some embodiments, the low surface energy material may comprise terpolymers prepared by the polymerization of both ethylene and propylene with optionally one or more additional diene Monomers, such as ethylidene norborane, dicyclopentadiene and/or hexadiene.

In some embodiments, the low surface energy material may comprise polybutenes including, but not limited to polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio.

In some embodiments, the low surface energy material is covalently attached to said assembly. In some embodiments, the low surface energy material is non-covalently associated with said assembly.

In some embodiments, the low surface energy material is modified via exposure to a nucleophile or an electrophile, which modifies the material so that it can form a bond or association with the nanowire assembly.

In some embodiments, the coated assemblies further comprise coloring agents, anti-oxidants, surfactants, contrast agents, water resistant agents, bleaching agents, abrasive agents, flame retardants, drugs, such as antimicrobials, compounds used in treating coronary artery disease or atherosclerosis, In some embodiments, the coated assemblies further comprise anesthetics, chemotherapeutic agents, immunotoxins, immunosuppressive agents, steroids, antibiotics, antivirals, antifungals, steroidal antiinflammatories, anticoagulants, antiproliferative agents, angiogenic agents, anti-angiogenic agents, or combinations thereof. In some embodiments, the the coated assemblies further comprise a hydrophobic drug such as rapamycin, paclitaxel, dexamethasone, lidocaine, retinoic acid, estradiol, pimecrolimus, tacrolimos, tetracaine or combinations thereof.

In embodiments, various types of deposition techniques can be used to deposit the low surface energy material and/or other compounds which comprise the coatings as described herein, on the nanowire assemblies including, but not limited to oxidation, nitridation, chemical vapor deposition (CVD), plasma enhanced chemical vapor deposition (PECVD), sputtering, spraying, dip coating, e-beam evaporation, spin coating, roll-to-roll coating, or any combination thereof. Other coating methods may be employed as well.

Coating of the assemblies of this invention, in some embodiments, produces a superhydrophobic assembly.

In one embodiment of this invention, the coated assembly may exhibit a water contact angle of above 160°. In another embodiment, the coated assembly may exhibit a water contact angle of about 163°. In another embodiment, the coated assembly may exhibit a water contact angle of between 160°-465°. In is another embodiment, the coated assembly may exhibit a water contact angle of between 150°-160°. In another embodiment, the coated assembly may exhibit a water contact angle of between 160°-165°. In another embodiment, the coated assembly may exhibit a water contact angle of between 160°-170°. In another embodiment, the coated assembly may exhibit a water contact angle of between 160°-175°.

In one embodiment of this invention, the coated assembly may exhibit a water contact angle hysteresis of between 10°-15°. In another embodiment the coated assembly may exhibit a water contact angle hysteresis of between 10°-14°. In another embodiment, the coated assembly may exhibit a water contact angle hysteresis of between 8°-13°. In another embodiment, the coated assembly may exhibit a water contact angle hysteresis of between 6°-12°. In another embodiment, the coated assembly may exhibit a water contact angle hysteresis of between 5°-10°. In another embodiment, the coated assembly may exhibit a water contact angle hysteresis of between 0°-5°.

In one embodiment of this invention, the coated assemblies of this invention comprise an assembly exhibiting pore sizes of between 0.01-100 micron. In another embodiment, the assembly may exhibit pore sizes of between 0.1-100 micron. In another embodiment, the assembly may exhibit pore sizes of between 0.1-50 micron. In another embodiment, the assembly may exhibit pore sizes of between 0.1-10 micron. In 30 another embodiment, the assembly may exhibit pore sizes of between 0.1-5 micron. In another embodiment, the assembly may exhibit pore sizes of between 0.1-2 micron. In another embodiment, the assembly may exhibit pore sizes of between 0.2-1.5 micron. In another embodiment, the pore size may be non-uniform. In another embodiment, the pore size may be uniform.

In another embodiment, other materials may be incorporated within the assemblies of this invention, for example, and in one embodiment, other metals may be incorporated within the assemblies, and may, in some embodiments, specifically be incorporated in the pores formed by the network of nanowires.

In one embodiment of this invention, the diameter of the nanowires, or, in another embodiment, nanowires in the assembly, which in some comprise only some nanowires, or in other embodiments comprises nanowires mostly having a diameter of between 1 nm-5 micron, or in another embodiment, the diameter is between 1 nm-500 nm, or in another embodiment, the diameter is between 1 nm-100 nm, or in another embodiment, the diameter is between 100 nm-1000 nm, or in another embodiment, the diameter is between 1000 nm-5000 nm.

In one embodiment of this invention, the nanowires are coated with a material, wherein the surface energy of the material is below 5 $mJ/m^2$. In one embodiment of this invention, nanowires are coated with a material, wherein the surface energy of the material is below 1 $mJ/m^2$. In another embodiment, the surface energy of the material is between 0.1-1 $mJ/m^2$. In another embodiment, the surface energy of the material is between 0.1-0.5 $mJ/m^2$. In another embodiment, the surface energy of the material is between 0.5-0.9 $mJ/m^2$.

In one embodiment, the coating is on at least a part of at least one surface of the assembly. In one embodiment, the coating covers an entire surface of the assembly. In one embodiment, the coating covers all exposed surfaces of the assembly. In some embodiment, the coating covers more than about 50%, or in another embodiment, more than about 60%, or in another embodiment, more than about 70%, or in another embodiment, more than about 75%, or in another embodiment, more than about 80%, or in another embodiment, more than about 85%, or in another embodiment, more than about 90%, or in another embodiment, more than about 95%, or in another embodiment, more than about 98%, of the exposed surfaces of the assembly. In some embodiments, the coating is applied in a particular pattern, to suit a particular purpose. In some embodiments, the coating is applied such that the underlying nanowire assembly is not exposed to the environment. In some embodiments, the coating is applied in multiple layers.

In one embodiment, the term "about" refers to a deviance from the stated value or range of values by +/−1%, or in another embodiment, by +/−2%, or in another embodiment, by +/−0.5%, or in another embodiment, by +/−7%, or in another embodiment, by +/−10%, or in another embodiment, by +/−13%, or in another embodiment, by +/−15%, or in another embodiment, by +/−18%, or in another embodiment, by +/−20%.

In some embodiments, the low surface energy material is covalently attached to said assembly, or in another embodiment, non-covalently associated with the assembly. Such attachment is achievable by various means known in the art, for example, as described and exemplified herein. In some embodiments, cross-linking agents may be employed, which attach or facilitate attachment of the low surface energy material to the assemblies of nanowires of this invention. Such materials are well known in the art, and may comprise zero length cross linking agents, and others, as will be appreciated by one skilled in the art. In some embodiments, the low surface energy material is functionalized such that its interaction with or binding to the assembly is promoted or facilitated.

In some embodiments, the assembly is thermostable. In some embodiments the assembly may be stripped and recoated two or more times.

In one embodiment, the coated assemblies of this invention are superhydrophobic. In one embodiment, the superhydrophobicity of the assemblies of this invention may be determined by static and dynamic contact angle measurements. In one embodiment, the superhydrophobicity of the assemblies of this invention may exhibit minimal to negligible contact angle hysteresis.

In some embodiments, this invention provides a process for the preparation of a coated, absorbent, freestanding assembly comprising inorganic nanowires, the process comprising:
hydrothermically synthesizing inorganic nanowires;
dispersing said nanowires in a polar solvent to form a suspension;
casting said suspension on a non-adherent substrate to form a freestanding assembly; and
coating said freestanding assembly with a low-surface energy molecule.

In some embodiments, the term "hydrothermically synthesizing" encompasses its art recognized meanings, and may refer to a process that involves heating the inorganic material with steam, or in an aqueous system and optionally under pressure, to form the nanowire structures. In some embodiments, the heat will be to a temperature of at least above 100° C.

In some embodiments, the nanowires self-assemble into bundles. In some embodiments, the nanowires and/or bundles self-assemble into an inter-penetrating, micro-porous network.

Construction of the desired nanowires and/or nanowire assemblies may be verified by a number of means in the art, including, inter alia, electron microscopy, or in another embodiment, by scanning electron microscopy (SEM), or in another embodiment, by tunneling electron microscopy (TEM), or in another embodiment, by optical microscopy, or in another embodiment, by atomic absorption spectroscopy (AAS), or in another embodiment, by X-ray powder diffraction (XRD), or in another embodiment, by X-ray photoelectron spectroscopy (XPS), or in another embodiment, by atomic force microscopy (AFM), or in another embodiment, by ICP (inductively coupled plasma).

In some embodiments of the process of this invention, the polar solvent is water. In some embodiment, the polar solvent is tetrahydrofuran, dimethylsulfoxide, ethanol, methanol, propanol, bunatol, (and similar alcohols) acetonitrile, acetone or water solutions with inorganic buffers and salts.

In embodiments, various types of coating techniques can be used to deposit the low surface energy material on the nanowire assemblies including, but not limited to oxidation, nitridation, chemical vapor deposition (CVD), plasma enhanced chemical vapor deposition (PECVD), sputtering, spraying, dip coating, e-beam evaporation, spin coating, roll-to-roll coating, or any combination thereof. Other coating methods may be employed as well.

In some embodiments casing is conducted on a teflon, or teflon coated substrate. In some embodiments the term "casting" refers to formation of the assembly solidification of the nanowire-containing suspension on a solid substrate. In one embodiment, the substrate is a mold, and casting in the mold facilitates the formation of a desired shape or geometry with the assembly. In some embodiments casting comprises drop casting, where the nanowire suspension is deposited on a solid substrate or within a mold, and solvent evaporation forms the desired assembly. In some embodiments, the choice in materials to form the nanowires is such that the resulting free-standing assembly is superhydrophobic, and in some embodiments, highly absorptive.

In another embodiment casting comprises spin casting, which deposits the nanowire suspension onto a solid substrate, which is then spun at high speeds (for example around 3000 rpm). In some embodiments, the centripetal acceleration facilitates spreading of the suspension as it dries, and a thin film/paper is then formed on the surface of the substrate.

In some embodiments, the assembly properties, for example, shape and thickness may vary, and in some embodiments, are a function of, for example, the nature of the nanowire suspension, the parameters chosen for the spin process, or other casting, or others, or any combination thereof.

In some embodiments, the process comprises removal or evaporation of liquids during the formation of the assembly.

In some embodiments the solid substrate and/or mold used in casting may comprise any non-adherent material, for example, silicon, rubber, teflon or ceramics.

In some embodiments, casting involves formation of a paper or foil comprising the nanowire assembly.

In some embodiments, coating may employ various implements, such as masks, or other materials for specific or localized deposition, or deposition according to a pattern or design. Coating will comprise deposition on at least a portion of a surface of the nanowire assembly, and may be according to any design or geometry, for example, to suit a particular application.

In some embodiments, the coating results in a covalent attachment of the low-surface energy molecule to a surface of the assembly or non-covalent association with the assembly.

In one embodiment, the assembly is coated with the low surface energy material on a surface distal to the surface in contact with the material. In one embodiment, the proximal surface in contact with the material is bonded to the material.

In one embodiment of this invention, the assembly is so treated or constructed so as to exhibit surface roughness properties, prior to coating. Such modification may enhance the superhydrophobicity of the assembly, as exemplified herein with an $MnO_2$ nanowire paper heated at 600° C., which introduced nanoscale point defects on the surface of the nanowires while the free-standing structure remains largely intact.

In some embodiments, the process further comprises stripping of the coating, and subsequent reapplication of the coating, which in some embodiments may be accomplished two or more times. In some embodiments, the stripping of the coating is accomplished by ultrasonication, application of a temperature of at least 300° C., or a combination thereof. In some embodiments, stripping may comprise application of electric current or UV irradiation.

In some embodiments, the assemblies of this invention are environmentally friendly, in that they may be reused, repeatedly. In some embodiments, the removal of adsorbed contaminants to the assemblies of this invention provide an environmentally friendly means of removal. For example, application of heat to the assemblies of this invention for removal of an organic from a contaminated water source provides for localized concentration of the contaminant, cleansing of the water supply, and provides a reusable material for further decontamination processes.

In one embodiment, the assemblies of this invention are self-supporting structures, with a controllable, or high porosity, controllable or high-surface-area interior, thermal stability, or a combination thereof, in additional to their superhydrophobicity. In some embodiments, these characteristics are utilized for any appropriate method or application, for example, the absorbent capacity and hydrophobic nature of the assemblies may find application in inter alia, use of the assemblies as an absorbent material in the removal of organics.

Such application is exemplified herein, for example in FIG. 4. According to this embodiment, superhydrophobic $MnO_2$ nanowire paper showed high uptake capacities for a collection of organic solvents and oils. This embodiment of the nanowire paper readily adsorbed the gasoline layer. Moreover, the nanowire paper was regenerated after use by ultrasonication and autoclaving (~130° C. for 20 min), thus in some embodiments, the assemblies of this invention can sustain relatively high operating temperatures (~380° C.), which are several times higher than those of the conventional polymer membrane adsorbent materials (~60° C.).

In some embodiments, such assemblies may be useful in the construction of filters and applied to the synthesis or preparation of pharmaceutical products or formulations, wherein the removal of an organic solvent is desired. In some embodiments, the assemblies of this invention will have exquisite sensitivity for removal of the organic solvents from such preparations, to produce purified pharmaceutical preparations, where only trace, or no detectable organic solvent remains in the preparation or formulation. In one embodiment the organic solvent may include, inter alia, tetrahydrofuran, diethylformamide, mono- or dichlorobenzene, or a combination thereof.

In one embodiment, this invention provides an article of manufacture comprising an assembly of this invention. In one embodiment, the article of manufacture may be, inter alia, a waterproof substance. In another embodiment, the article of manufacture may be, inter alia, a water resistant substance. In another embodiment, the article of manufacture may be, inter alia, a self-cleaning substance. In another embodiment, the article of manufacture may be, inter alia, a water draining substance. In another embodiment, the article of manufacture may be, inter alia, a coating substance. In another embodiment, the coating substance reduces drag. In another embodiment, the coating substance reduces drag in a gas, in a liquid or in both. In another embodiment, the gas may be air. In another embodiment, the liquid may be water.

In another embodiment of this invention, the article of manufacture may be a membrane.

In another embodiment of this invention, the article of manufacture may be, inter alia, a fabric, or protective gear.

In one embodiment, the fabric may be, inter alia, a breathable fabric. In another embodiment, the fabric may have, inter alia, filtration functionality. In another embodiment, the fabric may have, inter alia, an absorptive functionality. In another embodiment, the fabric may be, inter alia, a waterproof fabric. In another embodiment, the fabric may be, inter alia, a water resistant fabric.

In one embodiment of this invention, the fabric may be a superhydrophobic fabric. In one embodiment of this invention, the article of manufacture, such as, for example, a fabric may exhibit a water contact angle of above 160°. In another embodiment, the article of manufacture, such as, for example, a fabric may exhibit a water contact angle of about 163°. In another embodiment, the article of manufacture, such as, for example, a fabric may exhibit a water contact angle of between 160°-465°. In another embodiment, the article of manufacture, such as, for example, a fabric may exhibit a water contact angle of between 150°-160°. In another embodiment, the article of manufacture, such as, for example, a fabric may exhibit a water contact angle of between 160°-165°. In another embodiment, the article of manufacture, such as, for example, a fabric may exhibit a water contact angle of between 160°-170°. In another embodiment, the article of manufacture, such as, for example, a fabric may exhibit a water contact angle of between 160°-175°.

In some embodiments, this invention provides an article of manufacture comprising an assembly of this invention.

In another embodiment of this invention, the article of manufacture may be, inter alia, a drug delivery system. In another embodiment, the article of manufacture may be, inter alia, a bandage or patch. In another embodiment, the bandage or patch may include, inter alia, a drug.

In some embodiments, this invention provides a device, apparatus or apparel comprising an assembly of this invention. In some embodiments, the device is a filter or a membrane.

In some embodiments, the assemblies of this invention find application in decontaminating, and/or detoxifying fluids and/or concentrating contaminants. In one embodiment, the assemblies of this invention find application in the treatment of toxic waste products. In another embodiment, the assemblies of this invention find application in the treatment of effluents resulting from industrial production of various chemical compounds, or pharmaceuticals. In another embodiment, the assemblies of this invention find application in the treatment of water supplies (rivers, streams, sea water, lake water, groundwater, etc.) contaminated by chemical compounds or toxic materials. In another embodiment, the assemblies of this invention find application in the treatment of toxic waste products due to occurrence of a natural disaster. In another embodiment, the assemblies of this invention find application in the treatment of petroleum spills. In another embodiment, the assemblies of this invention find application in the treatment of environmental pollutants. In another embodiment, the assemblies of this invention find application in the decontamination of water. In another embodiment, the assemblies of this invention find application in the decontamination of chemical reactions. In another embodiment, the assemblies of this invention find application in the decontamination of organic solvents. In another embodiment, the assemblies of this invention find application in the decontamination of air. In another embodiment, the assemblies of this invention find application in the decontamination of gases. In another embodiment, the assemblies of this invention find application in the decontamination of weapons of mass destruction (W.M.D), or in another embodiment, biological, virus, and/or chemical (including gas and liquid) weapons. In another embodiment, the assemblies of this invention find application in the decontamination of oil tankers, transport containers, plastic containers or bottles. In another embodiment, the assemblies of this invention find application in the decontamination of soil. In another embodiment, the assemblies of this invention find application in the decontamination of filters, for example, air purification and air-conditioning filters.

In one embodiment, the term "decontaminating" refers to degrading, eliminating, removing, or isolating, in whole or in part, a substance whose degradation, elimination, removal or isolation is desired. In some embodiments, the term "decontaminating" is to be considered as encompassing the terms "detoxifying" and/or "sanitizing".

In some embodiments, this invention provides a method of purifying a fluid contaminated with organic materials, the method comprising contacting a solution contaminated with one or more organic materials with a coated assembly of this invention.

In one embodiment, the assemblies, devices, apparatuses and/or methods of this invention decontaminate fluids, by contacting the fluid with the assemblies, or devices, or apparatuses, or articles of manufacture, etc., of this invention. In one embodiment, the term "contacting" refers to direct contact, such as, for example, placement of each within a single vesicle or chamber. In one embodiment, the term "contacting" refers to indirect exposure, for example, using a series of relays which convey the fluid to a chamber or vesicle, or tube, or a means of containment, wherein the two are in contact with each other, or convey the contaminated fluid to a device, apparatus, etc., comprising an assembly of this invention. In one embodiment, the term "contacting" refers to a process of mixing, or reacting, or agitating, or shaking, or bubbling, etc. In one embodiment, the term "contacting" refers to bubbling or mixing of gases in aqueous solution, in which the assemblies of this invention are contained. In one embodiment, the chamber wherein the two are contacted may comprise a means of mixing/agitating the components, such as positioning on a stirring device, in the presence of for example, a stir bar. In another embodiment, the term "mixing" is to be understood as encompassing the optional application of a magnetic field, heat, microwaves, ultraviolet light and/or ultrasonic pulses, to accelerate the mixing of the materials. In another embodiment, the term "mixing" is to be understood as encompassing the improving of the yield of the process by the application of stirring, shaking and optionally application of a magnetic field, heat, light, microwaves, ultraviolet light and/or ultrasonic pulses.

According to this aspect and in one embodiment, the method comprises use of a filter or membrane comprising a coated assembly of this invention.

In some embodiments, the material whose decontamination is desired may comprise poisonous, harmful substances, noxious chemicals, undesired pharmaceuticals, toxins, undesirable reaction by-products, pollutants, poisonous gas, or radioactive materials. In some embodiments, the term "decontaminating" refers to the conversion, in whole or in part, of an environmental contaminant to a substance less toxic than the environmental contaminant.

In some embodiments, the device, apparatus or apparel of this invention is for use for a described method or application herein. For example, and in some embodiments, the device may comprise a decontamination device, equipped with, for example, filters comprising the assemblies of this invention, for decontamination or isolation of a particular material.

In one embodiment, this invention provides a decontamination kit comprising a coated assembly of this invention.

In one embodiment, the term "kit" refers to a packaged product, which comprises the coated assemblies of this invention, or in some embodiments, the materials for the preparation of coated nanowires, including the materials for the construction of the nanowires and coating material therefor, at pre-determined ratios and concentration, for use in the decontamination of a specified fluid, for which the use of the kit has been optimized, as will be appreciated by one skilled in the art.

In one embodiment, the choice of coated assembly will depend upon the indicated use for decontaminating a particular compound, for example, for fluids comprising hydrocarbon-based fuel contaminants, effluents formed as a result of a particular chemical process, pharmaceutical process, etc.

In one embodiment, the kit will contain instructions for a range of uses of the individual components, which may be present in the kit at various concentrations and/or ratios, in individually marked containers, whereby the end-user is provided optimized instructions for use in a particular application.

In one embodiment, the kits are comprised of agents whose composition and/or concentration are optimized for the types of contaminants for which the kits will be put to use, for example, for various hydrocarbon-contaminated fluids. In another embodiment, the kits are comprised of agents whose composition and/or concentration are optimized for use in a particular environment, for example, for the decontamination of a water supply adjacent to chemical factories, which produce various solvents or toxins.

In one embodiment, the kits may be stored for prolonged periods of time at room temperature. In one embodiment, the kits may additionally comprise an indicator compound, which reflects partial or complete decontamination, or removal of the contaminant.

In one embodiment, the terms "a" or "an" as used herein, refer to at least one, or multiples of the indicated element, which may be present in any desired order of magnitude, to suit a particular application, as will be appreciated by the skilled artisan. In one embodiment, the term "a coated assembly" refers to two or more kinds of coated assemblies, which differ in terms of their composition, or in one embodiment, size, or in one embodiment, surface modification, or a combination thereof, or other qualitative differences as will be understood by one skilled in the art, as well as referring to the inclusion of multiples of the identical type, size, etc., coated assembly. In some embodiments, the assemblies, kits and methods of this invention may comprise and/or make use of multiple kinds of coated assemblies for the indicated applications, e.g. decontaminating a fluid comprising multiple contaminants, in one embodiment, or a single contaminant, in another embodiment, or preventing water damage or corrosion, or other applications, as described herein, and as understood by one skilled in the art.

In some embodiments, this invention provides a method of waterproofing a material, comprising surrounding, coating or applying the coated assemblies of this invention to the material.

In some embodiments, the assembly is coated with the low surface energy material on a surface distal to that in contact with the material whose waterproofing is desired. In some embodiments, the proximal surface of the assembly, which is in contact with the material is bonded to the material.

In some embodiments, the material is a food or pharmaceutical product. In some embodiments, the material is a machinery or apparel which is submerged in water.

In some embodiments, the material is subjected to high water pressure.

In some embodiments, the material is a device, or a component thereof, for example, a fluidic pump, whose corrosion, or destruction or impairment is reduced by incorporating the assemblies of this invention.

In some embodiments, whole devices are encased in the coated assemblies of this invention, for example, electronic equipment, or equipment, which in the course of its operation may come into contact with water and which may be damaged thereby. In such applications, the strength and waterproofing capacity of the assemblies of this invention may be utilized to construct appropriate casing for such devices. Such devices may comprise computers or electronics, timepieces, data storage materials, or cases for the same, hygroscopic materials, etc. as will be appreciated by one skilled in the art. Similarly, materials, which are combustible when in contact with a particular hydrophilic material or fluid may be contained within a packaging material or device coated with or prepared with a coated assembly of this invention to prevent such contact.

In some embodiments, apparel may similarly be constructed and utilized. In some embodiments, such apparel may be resistant to effects of water pressure, and may thus find application in the assembly of diving apparel or equipment, as well as in machinery or other apparatuses, on any scale, which are exposed to water and moderate to high water pressure for extended periods of time, as will be appreciated by one skilled in the art.

In some embodiments, such apparel may serve as protective gear for individuals coming into contact with noxious organic solvents, for example, such as gear for environmental containment procedures, or chemical warfare clean up, for example, and include the preparation of outerclothing, filtering devices, goggles, etc.

In one embodiment, this invention provides a method of waterproofing a material, the method comprising surrounding or coating the material with a coated assembly of this invention.

In one embodiment, the material is a food or pharmaceutical product, and the assemblies of this invention encase such products. For example, in some embodiments, the assemblies of this invention may find application in the preparation of a packaging material for a food or pharmaceutical product. In some embodiments, the external surface, that is in contact with the environment is coated with a low surface material as herein described, thus preventing or diminishing contact with water or other environmental materials with that which is contained within the packaging material. In some embodiments, the interior of the packaging material is coated with an inert material, which is not hazardous for human consumption.

The assemblies of this invention may be utilized to prepare a variety of medical devices, as well. Such assemblies may be utilized for the coating of endoscopes, catheters, appliances, surgical tools, or other materials inserted into a subject, wherein adhesion with fascia or other body tissues or materials is not desirable. The choice of coating material in such embodiments, will reflect a material with minimal or no toxicity when in contact with human tissue.

In some embodiments, the coated assemblies may comprise or be used to coat any insertable or implantable medical instruments or devices including guide wires, catheters, dilatation balloons, stents, stent grafts, grafts, vena cava filter, inflation lumens and so forth.

In some embodiments, devices which make use of the assemblies of this invention may comprise drug-delivering vascular stents (e.g., self-expanding stents typically made from nitinol, balloon-expanded stents typically prepared from stainless steel); other vascular devices (e.g., grafts, catheters, valves, artificial hearts, heart assist devices); implantable defibrillators; blood oxygenator devices (e.g., tubing, membranes); surgical devices (e.g., vertebral disks, bone pins, hemostatic barriers, clamps, screws, plates, clips, vascular implants); membranes; shunts for hydrocephalus; endoscopic devices; infection control devices; dental devices (e.g., dental implants, fracture repair devices), urological devices (e.g., penile, sphincter, urethral, bladder and renal devices, and catheters); colostomy bag attachment devices; ophthalmic devices (e.g. ocular coils); glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts).

Examples of useful devices include urinary catheters (e.g., surface-coated with antimicrobial agents such as vancomycin or norfloxacin), intravenous catheters (e.g., treated with antithrombotic agents (e.g., heparin, hirudin, coumadin), small diameter grafts, vascular grafts, artificial lung catheters, atrial septal defect closures, glucose sensors (long-term and short-term), coronary stents (e.g., degradable, non-degradable, peripheral), blood pressure and stent graft catheters, birth control devices, benign prostate and prostate cancer implants, breast implants, dental implants, implanted drug infusion tubes, intravitreal drug delivery devices, nerve regeneration conduits, oncological implants, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stems/implants, in vitro diagnostics, aneurysm exclusion devices, and neuropatches.

Examples of other suitable devices include, but are not limited to, vena cave filters, urinary dialators, endoscopic surgical tissue extractors, atherectomy catheters, clot extraction catheters, percutaneous transluminal angioplasty catheters, PTCA catheters, stylets (vascular and non-vascular), coronary guidewires, drug infusion catheters, esophageal stems, circulatory support systems, angiographic catheters, transition sheaths and dilators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, elechrophysiology catheters, stroke therapy catheters, abscess drainage catheters, biliary drainage products, dialysis catheters, central venous access catheters, and parental feeding catheters.

Examples of medical devices suitable for the present invention include, but are not limited to catheters, implantable vascular access ports, blood storage bags, vascular stems, blood tubing, arterial catheters, vascular grafts, inbraaortic balloon pumps, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs, as well as filters adapted for deployment in a blood vessel in order to trap emboli.

In addition, the assemblies may be utilized as a means of fishing out, diminishing or preventing lipid accumulation in a subject. In some embodiments, this invention provides a method of diminishing or abrogating lipid accumulation in a blood vessel in a subject, comprising inserting a removable assembly of this invention in a blood vessel for a period of time sufficient for lipid accumulation on the assembly and removing the assembly. In some embodiments, the assembly is coated with a superhydrophobic, yet non-toxic material, which is highly adsorbent, and is implanted in subjects at risk for coronary artery disease. In one embodiment, for example, a removable coated catheter is inserted into one or more vessels at risk for lipid accumulation. The coated catheter is kept within the subject's vessels for a period of time sufficient to promote adhesion of the lipid to the catheter, as opposed to the vessel. Such treatment may be accompanied by diet modification and/or the administration of an agent, which stimulates digestion or release of a lipid from blood vessel walls, thereby reducing atherosclerosis in the subject.

In one embodiment the invention provides for fuel cells comprising the coated assemblies of this invention, wherein the fuel cells may be utilized for reversible storage of hydrogen. In one embodiment, hydrogen may be embedded in/attached to the assemlbies of this invention. In one embodiment, the term "fuel cell" refers to an electrochemical cell in which the energy of a reaction between a fuel, such as hydrogen, and an oxidant, such as oxygen, is converted directly and continuously into electrical energy.

In some embodiments, the coated assemblies of this invention may be useful in the crystallization of a drug or other desired molecules, for example, various proteins. In some embodiments, the coated assemblies may be useful, in some embodiments, as a solid support, for catalysis reactions, or in other embodiments, may comprise a catalyst and participate in catalysis.

The following examples are presented in order to more fully illustrate some embodiments of the invention. They should, in no way be construed, however, as limiting the scope of the invention.

EXAMPLES

Materials and Methods

[Please Provide Methods, Settings, Etc. For EM, EDS and X-Ray Powder Diffraction Procedures or a Reference]

Example 1

Superhydorphillic Absorbent Freestanding Assemblies

Cryptomelane-type manganese oxide (MnO2) nanowires were first synthesized at 250° C. in an autoclave in the presence of stoichiometric mixtures of potassium sulfate, potassium persulfate, and manganese sulfate monohydrate (J. Yuan, et al., Adv. Mater. 16, 1729 (2004)). This hydrothermal treatment yielded a wool-like suspension after dispersing the nanowires in deionized water overnight. The water was removed by casting the suspension on a Teflon substrate placed in an oven, resulting in self-assembled nanowire membrane production. The paperlike membranes were peeled off from the underlying substrate.

Free-standing nanowire paper of arbitrary size and shape, that exhibits a uniform surface morphology can be readily synthesized via this approach, and represents embodiments of this invention.

The crystallographic phase of the $Mn_2O_3$ nanowires was determined by powder XRD (Rigaku RU300, CuKα radiation). TEM images were recorded on a field-emission JEM-3000F high-resolution transmission electron microscope operated at 300 kV and equipped with an energy-dispersive X-ray spectrometer. Surface morphology of the nanowire paper was observed using a JEOL-5910 scanning electron microscope. Sessile drop contact angle measurements were performed by adding water to the sample surface with a motor-driven syringe. The advancing ($θ_A$) and receding ($θ_R$) angles were obtained by extending and contracting the volume of the drop, respectively.

Figure 1B:
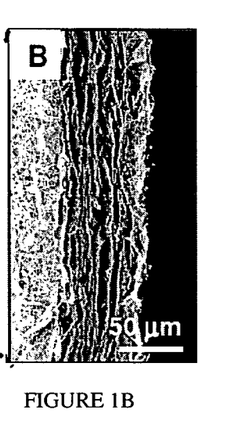
Figure 1C:
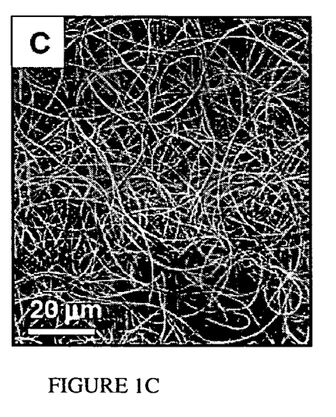
Figure 1D:
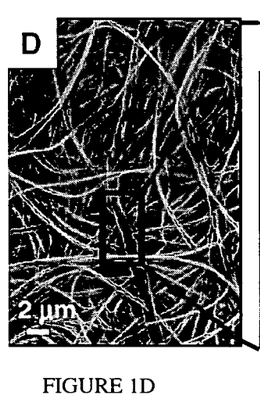
Figure 1E:
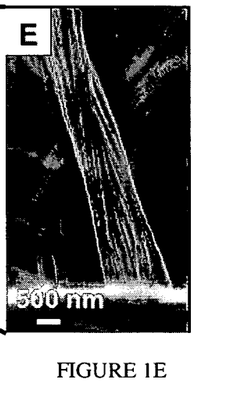
Figure 1F:
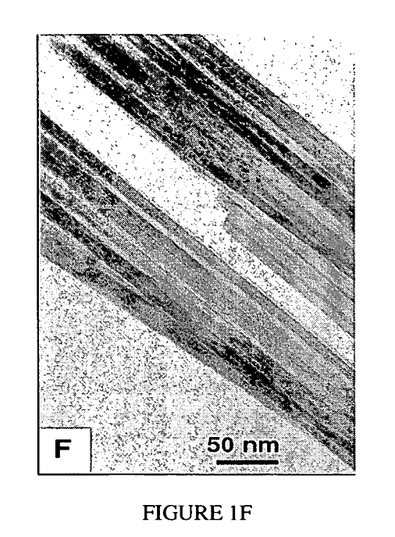
Figure 1G:
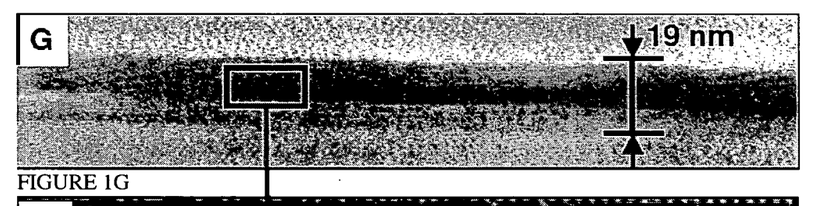
Figure 1H:
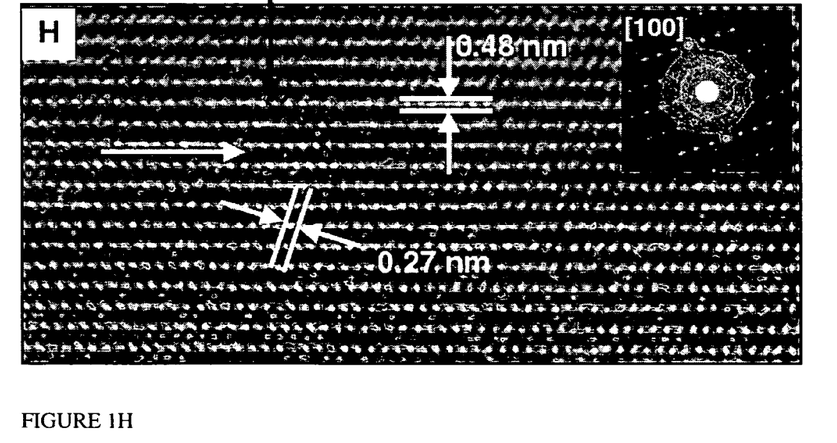

One embodiment of a nanowire paper of this invention, having a 27-cm edge length is shown in FIG. 1A. Scanning electron microscopy (SEM) images provide details on its hierarchical structure. FIG. 1B shows a cross-sectional view of the nanowire paper consisting of multiple layers (~50 μm thick) nanowire assemblies. Another striking feature is that a large portion of nanowires self-assemble in bundles over a length scale longer than several hundred of micrometers and inter-penetrate within the membrane structure to form a micro-porous network (FIG. 1C-E). The average length of the individual nanowires is about 0.6 mm measured by aligning the nanowires in one orientation (19). A transmission electron microscopy (TEM) image representing the general morphology of the MnO2 nanowires is shown in FIG. 1F. It reveals that the nanowires are straight with uniform morphology. FIG. 1G shows the high-magnification TEM image of a single nanowire with a uniform diameter (~19 nm) along its long axis direction. The selected-area electron diffraction (SAED) pattern (upper right inset, FIG. 1H) of the nanowire can be indexed in accord with the [100] zone axis of a cryptomelane-M type (K2-xMn8O16) crystal (Joint Committee on Powder Diffraction Standards file no. 44-1386: a=9.942 Å, b=2.866 Å, c=9.709 Å). As shown the high-resolution TEM (HRTEM) image of the nanowire in FIG. 1H, the lattice fringes of the {002} and {011} with a d-spacing of 0.48 nm and 0.27 nm, respectively, for the monoclinic K2-xMn8O16, can be clearly seen. Within this nanowire, the [001] crystallographic direction is closely parallel to the long axis direction of the nanowire; no dislocations or stacking faults are observed in all areas examined within this nanowire crystal.

Figure 1I:
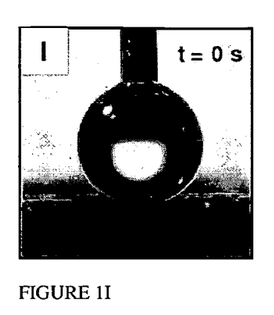
Figure 1J:
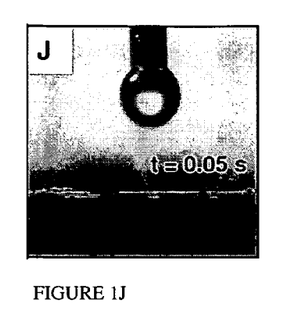

The $MnO_2$ nanowires form mixed-valent octahedral molecular sieves with one-dimensional tunnel structures, which make them ideal for adsorption of small molecules such as water. To examine the wettability of the nanowire paper, a video contact angle instrument was used and operated in dynamic mode at a capture speed of 60 frames/s (Figs. I and J). The wetting time for a water droplet (~1 μL) added to the surface is about 0.05 s. Interestingly, further addition of water droplets to the same location at a time interval of 120 s shows a remarkably consistent wetting time of 0.05 s in multiple tries (8 times) until water saturation point is reached at this specific location. The assembly was thus a hydrophilic material, owing to its contact angle of 0° and a consistent wetting time less than 0.1 s.

In contrast, the wetting time for a water droplet added to the surface of a thin film of $MnO_2$ nanoparticles (~20 nm) is about 0.16 s and the contact angle is close to 0°. The hierarchical micro- and nanoporous structure of the $MnO_2$ nanowire assembly may, in some embodiments, contribute to its enhanced superhydrophilicity when compared to the thin film structure of the nanoparticles.

Example 2

Superhydrophobic Adsorbent Free-Standing Assemblies

In order to determine whether the free-standing assemblies could be modified to prepare free-standing superhydrophobic materials, surface modification of the assemblies was undertaken. Toward this end, the nanowire paper was exposed to an organosilane atmosphere at 234° C. for 30 minutes.

A polydimethysiloxane (PDMS) stamp and the nanowire paper were placed in a sealed glass container. The coated nanowire paper exhibits a water contact angle of >170° C., which is indicative of full surface coverage. The coated assembly exhibited superhydrophobic characteristics, as evidenced by a high water contact angle of 172±1° (FIG. 2A) and a negligible hysteresis.

The superhydrophobic characteristic of the embodied assembly is unique, and in marked contrast to a variety of surfaces (mica, glass, and $MnO_2$ nanoparticle-coated glass) grafted with organosilanes. Mica is and glass substrates were cut into 0.5×0.5 $cm^2$ slides and sonicated sequentially in dichloromethane, methanol, and deionized water (Milli-Q) for 10 min. The wafers were then immersed in a freshly mixed ammonia peroxide solution ($H_2O$:$H_2O_2$:$NH_3 \cdot H_2O$ (v:v:v)=5:1:1) for 1 hour at about 90° C., after which time they were rinsed with deionized water followed by ethanol. The coatings of organosilanes on nanowire paper, mica and glass substrates were achieved by a vapor deposition technique. In a typical experiment, a polydimethysiloxane (PDMS) stamp and the nanowire paper were placed in a sealed glass container heated at 234° C. for 30 min. The coated nanowire paper exhibits a water contact angle of >170° C., which is indicative of full surface coverage.

The coated surfaces, in marked contrast to the superhydrophobic characteristic of the embodied assembly is unique, showed only moderate hydrophobic wetting behaviors and noticeable hystereses, as indicated by a contact angle range from 98° to 141°.

The dramatic wetting phase transition of the nanowire paper from absolute hydrophilic to superhydrophobic states may, in some embodiments, be attributable to its hierarchical structure.

Structural characterization of the organosilane-coated nanowire paper is shown in FIG. 2. FIG. 2B shows that self-assembled interpenetrating topologies of the nanowire paper remain unaltered, even after surface modification. The oriented nanowire bundle shown in FIG. 2B (Inset) and large amounts of air trapped in spaces in the micro- and nanoporous structures of the nanowire paper may contribute to the enhanced superhydrophobicity of the assembly. Such mechanism is a reflection of Cassie's law for a two-component system, wherein one component is air and having a contact angle of 180°, the effective contact angle $\theta_c$ is: $\cos \theta_c = f_1 \cos \theta_1 - f_2$, where $f_1$ is the area fraction of nanowires, $f_2$ is the area fraction of air trapped in the porous structures and $\theta_1$ is the contact angle of the organosilane.

Figure 2A:
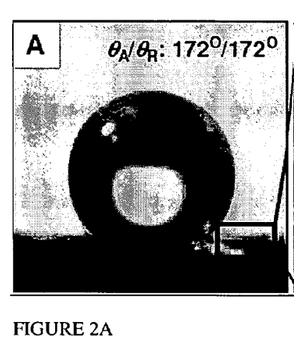
Figure 2B:
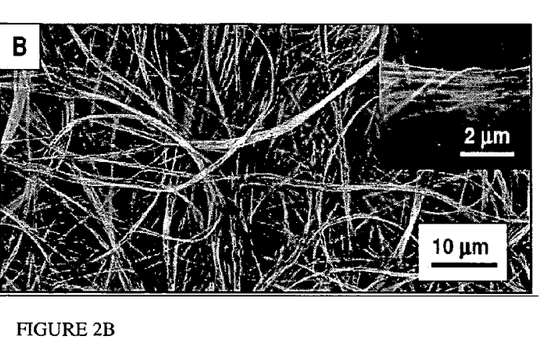
Figure 2C:
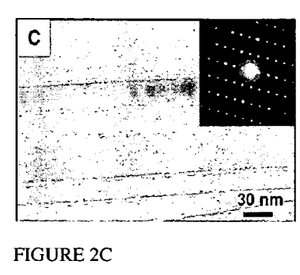
Figure 2D:
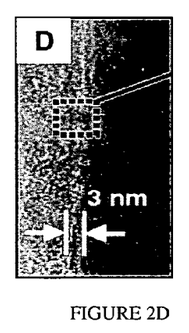
Figure 2E:
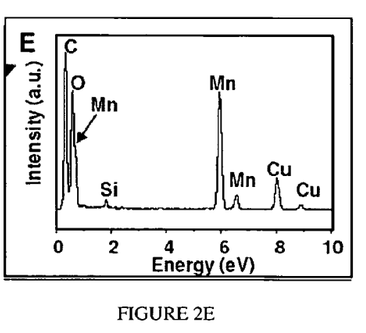

The coated nanowire structure was evaluated by transmission electron microscopy (FIG. 2C), which showed individual core-shell nanowires. The modified nanowires remained as single crystalline in structure, as characterized by the electron microdiffraction pattern (FIG. 2C, Inset) obtained from the individual nanowires. A high-magnification TEM image of an individual nanowire revealed that a conformal sheath (~3 nm) is formed on the surface of the nanowire. Composition analysis by energy-dispersive x-ray spectroscopy (EDS) on a selected area as shown in FIG. 2D indicated the shell structure of the nanowires comprised organosilanes (FIG. 2E).

Example 3

Recyclable Adsorbent Free-Standing Assemblies

Figure 2F:
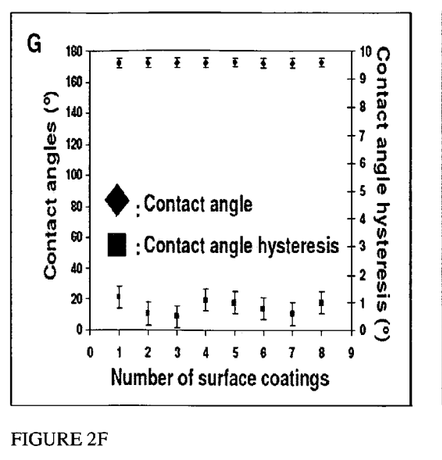
Figure 2G:
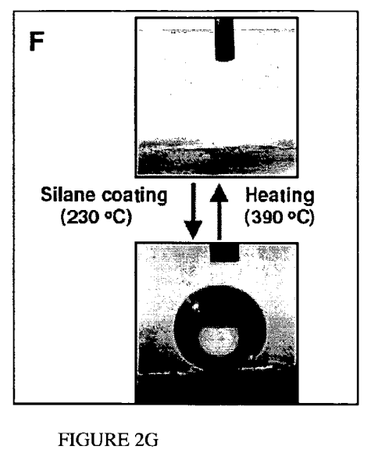

In order to determine whether the assemblies may be recycled, removal of the hydrophobic coating was explored by heating the nanowire paper at elevated temperatures (390° C., 30 minutes). Heating of the assembly resulted in reversible wetting behavior, with a return to a material more hydrophilic in nature, as opposed to the previous superhydrophobic state (FIG. 2F). These changes were reproducible cyclically, such that only subtle changes in water contact angles and hystereses were observed with each switching cycle (eight times for the study shown in FIG. 2G). Thus the coated assemblies of this invention provide a high degree of switching reversibility. Moreover, the coated assemblies herein described were found to be mechanically stable even after ultrasonic treatment.

Example 3

Other Embodiments of Adsorbent Free-Standing Assemblies

It was of interest to determine whether the superhydrophobicity of the nanowire assembly could be enhanced, by controlling its surface topologies.

Toward this end, the MnO$_2$ nanowire paper was heated at 600° C. in a furnace for 2 hours, during which time transformation of MnO$_2$ to Mn$_2$O$_3$ was induced, and nanoscale point defects occurred on the surface of the nanowires, however the free-standing structure remained largely intact.

Figure 3A:
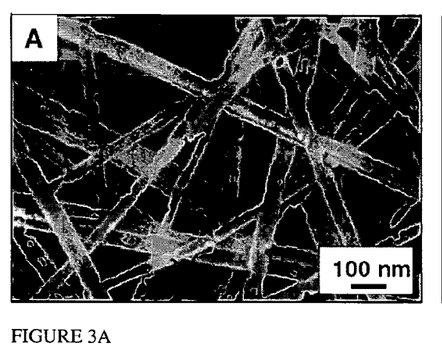
Figure 3B:
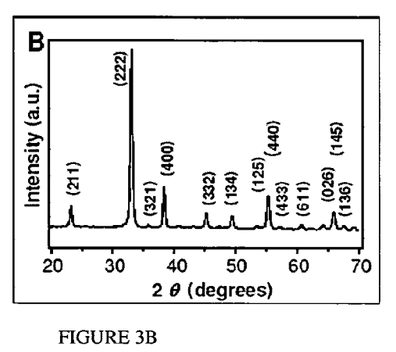
Figure 3C:
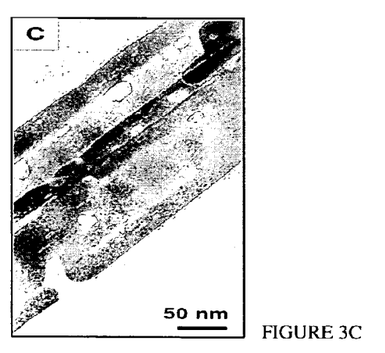
Figure 3D:
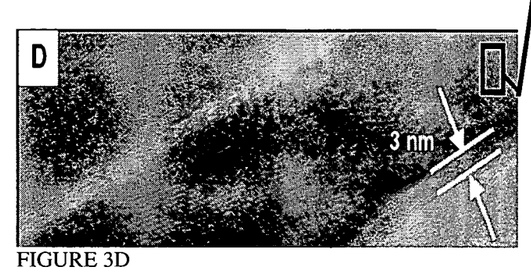

A representative SEM image of the nanowires with nanoscale defects is shown in FIG. 3A. X-ray powder diffraction analysis provided structural information and indicated crystallinity of the nanowires. As shown in FIG. 3B, all peaks can be assigned to diffraction from bixbyite-type Mn$_2$O$_3$. FIG. 3C demonstrated a high density distribution of line and point defects on the surface of the Mn$_2$O$_3$ nanowires, by TEM. TEM evaluation (FIG. 3D) also demonstrated a uniform coating over the surface of the Mn$_2$O$_3$ nanowire.

HRTEM analysis of the Mn$_2$O$_3$ nanowire (FIG. 3E), showed lattice fringes of the {200} planes with a d-spacing of 0.47 nm; an inset of ED pattern can be indexed to the [001] zone axis of a cubic Mn$_2$O$_3$ single crystal, as suggested by XRD spectrum.

Figure 3F:
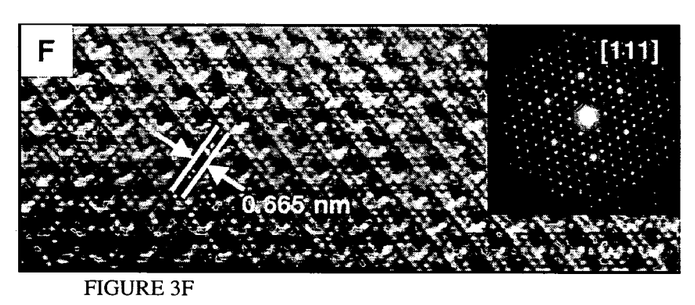

HRTEM image analysis of another Mn$_2$O$_3$ nanowire yielded a d-spacing of 0.665 nm, in agreement with those of the Mn$_2$O$_3$ (110) planes. The ED pattern (upper-right inset) can be assigned to the [111] zone axis pattern of the Mn$_2$O$_3$ crystal.

Figure 3G:
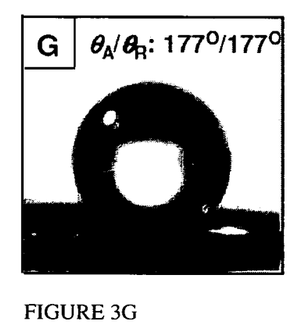

Subtle variations in surface topologies may be amplified into macroscopically detectable changes in wetting behavior. As shown in FIG. 3G, the organosilane-coated Mn$_2$O$_3$ nanowire paper exhibits enhanced superhydrophobic behavior as evidenced by high advancing and receding contact angles ($\theta A/\theta r=177°/177°$.

Example 4

Adsorbency of Free-Standing Assemblies

In order to determine whether the coated assemblies, in addition to having a self-supporting structure, porosity, high-surface-area interior, thermal stability, and superhydrophobicity were absorbent, absorption of hydrophobic materials onto the assembly was evaluated.

Figure 4A:
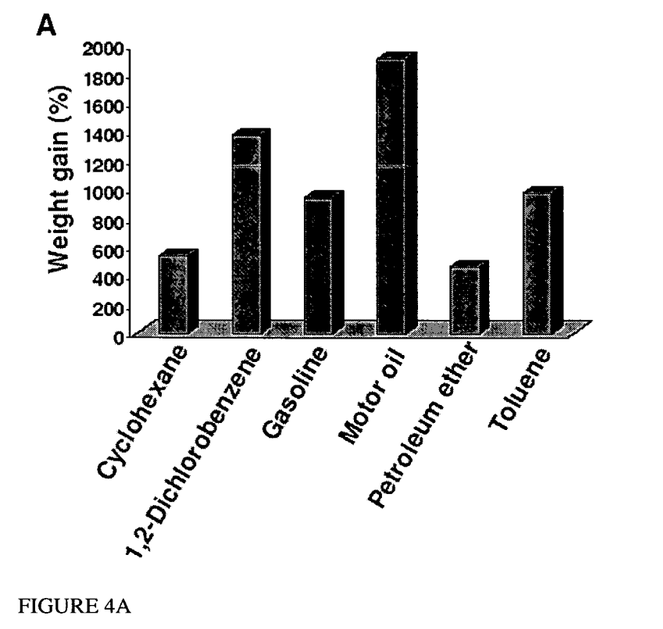
Figure 4B:
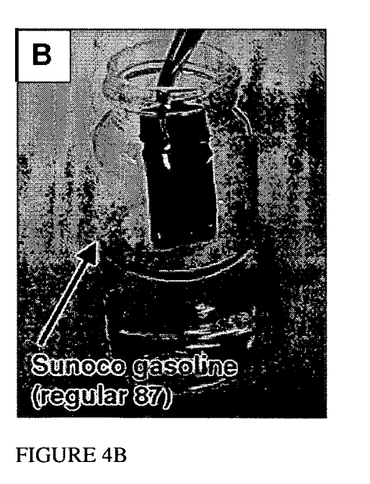
Figure 4C:
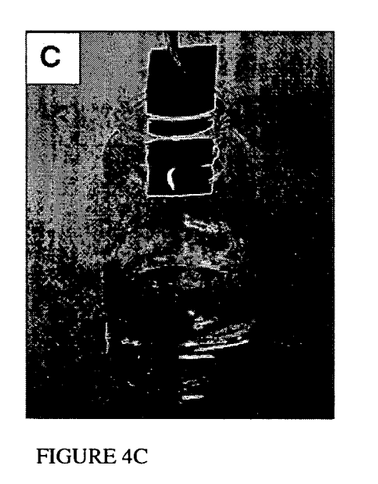

The superhydrophobic MnO$_2$ nanowire papers, representing an embodiment of the assemblies of this invention, were highly efficient in absorbing various organic solvents and oils (FIG. 4A). Moreover, immersion of a segment of the coated nanowire paper in a bi-phasic water sample comprising gasoline resulted in obvious adsorption of the gasoline to the paper (FIGS. 4B and C).

Taken together, these examples indicate that the coated inorganic absorbent nanowire free-standing assemblies of this invention can be recycled (e.g., following ultrasonication and autoclaving) and can sustain relatively high operating temperatures (~380° C.), which are several times higher than those of the conventional polymer membrane adsorbent materials (~60° C.).

These examples indicate that the wetting behavior of the coated inorganic absorbent nanowire free-standing assemblies of this invention can be controlled, e.g. from being absolutely hydrophilic to superhydrophobic.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What we claim is:

1. A method of purifying a fluid contaminated with hydrophobic organic materials, said method comprising contacting a solution contaminated with one or more hydrophobic organic materials with a coated, absorbent, freestanding assembly comprising inorganic nanowires, wherein said assembly is coated with a low surface energy material, and wherein said assembly may be stripped and recoated two or more times.

2. The method of claim 1, wherein said organic material is a petroleum based product.

3. The method of claim 1, wherein said organic material is an organic solvent.

4. The method of claim 1, wherein said nanowires have a diameter ranging from 1 nm to 1 micron.

5. The method of claim 1, wherein said nanowires are assembled in bundles and said bundles have a length of from about 200 micrometers to about 10 cm.

6. The method of claim 1, wherein said nanowires interpenetrate and form a micro-porous network, a nano-porous network, or a combination thereof.

7. The method of claim 1, wherein said inorganic nanowires comprise a metal oxide.

8. The method of claim 7, wherein said metal oxide is manganese oxide.

9. The method of claim 1, wherein said inorganic nanowires comprise a metal alloy.

10. The method of claim 1, wherein said assembly forms a paper or foil.

11. The method of claim 1, wherein said low surface energy material is an organosilane.

12. The method of claim 1, wherein said low surface energy material is a fluorocarbon based silane.

13. The method of claim 1, wherein said low surface energy material is covalently attached to said assembly.

14. The method of claim 1, wherein said assembly is superhydrophobic.

15. The method of claim 1, wherein said assembly is thermostable.

* * * * *